US012233276B2

(12) United States Patent
Rutzer et al.

(10) Patent No.: US 12,233,276 B2
(45) Date of Patent: Feb. 25, 2025

(54) AUTOMATIC LEAD SWITCHING

(71) Applicant: Physio-Control, Inc., Redmond, WA (US)

(72) Inventors: Mark Rutzer, Seattle, WA (US); Christina Mason, Renton, WA (US); David J. Linville, Woodinville, WA (US); Jason W. Fouts, Bothell, WA (US)

(73) Assignee: Physio-Control, Inc., Redmond, WA (US)

( * ) Notice: Subject to any disclaimer, the term of this patent is extended or adjusted under 35 U.S.C. 154(b) by 503 days.

(21) Appl. No.: 17/540,955

(22) Filed: Dec. 2, 2021

(65) Prior Publication Data

US 2022/0176138 A1 Jun. 9, 2022

Related U.S. Application Data

(60) Provisional application No. 63/121,107, filed on Dec. 3, 2020.

(51) Int. Cl.
*A61N 1/39* (2006.01)

(52) U.S. Cl.
CPC ......... *A61N 1/3993* (2013.01); *A61N 1/3904* (2017.08); *A61N 1/3943* (2013.01)

(58) Field of Classification Search
CPC ... A61N 1/3993; A61N 1/3904; A61N 1/3943
See application file for complete search history.

(56) References Cited

U.S. PATENT DOCUMENTS

| | | |
|---|---|---|
| 4,164,215 A | 8/1979 | Finlayson et al. |
| 7,818,058 B2 | 10/2010 | Mentelos |
| 8,190,223 B2 | 5/2012 | Al-Ali et al. |
| 8,226,543 B2 | 7/2012 | Tan et al. |
| 8,721,541 B2 | 5/2014 | Al-Ali et al. |
| 8,831,719 B2 | 9/2014 | Sullivan et al. |
| 9,604,069 B2 | 3/2017 | Helfenbein et al. |
| 9,630,016 B2 | 4/2017 | Wakabayashi et al. |
| 9,848,826 B2 | 12/2017 | Volpe et al. |
| 2014/0148869 A1* | 5/2014 | Stickney .......... A61N 1/046 607/142 |
| 2016/0220833 A1* | 8/2016 | Tan .................. A61B 5/11 |
| 2018/0291939 A1* | 10/2018 | Shetty .............. A61B 90/92 |

* cited by examiner

*Primary Examiner* — Joseph M Dietrich
(74) *Attorney, Agent, or Firm* — McDonnell Boehnen Hulbert & Berghoff LLP

(57) ABSTRACT

An example method is performed by a defibrillator that includes a therapy cable receptacle and an electrocardiogram cable receptacle. The method includes displaying a user interface screen that includes a primary channel for displaying a primary waveform and a secondary channel for displaying secondary data. The method also includes detecting a lack of a patient connection for therapy pads and detecting a patient connection for an ECG lead obtained using an ECG electrode cable. In addition, the method includes displaying a representation of an ECG signal obtained using the ECG electrode cable in the primary channel based on detecting the lack of the patient connection for the therapy pads and detecting the patient connection for the ECG lead.

20 Claims, 10 Drawing Sheets

1000

DISPLAYING, BY A DEFIBRILLATOR, A USER INTERFACE SCREEN THAT INCLUDES A PRIMARY CHANNEL FOR DISPLAYING A PRIMARY WAVEFORM AND A SECONDARY CHANNEL FOR DISPLAYING SECONDARY DATA — 1002

DETECTING, BY THE DEFIBRILLATOR, A LACK OF A PATIENT CONNECTION FOR THERAPY PADS — 1004

DETECTING, BY THE DEFIBRILLATOR, A PATIENT CONNECTION FOR AN ECG LEAD, WHEREIN THE ECG LEAD IS OBTAINED USING AN ECG ELECTRODE CABLE — 1006

BASED ON DETECTING THE LACK OF THE PATIENT CONNECTION FOR THE THERAPY PADS AND DETECTING THE PATIENT CONNECTION FOR THE ECG LEAD, DISPLAYING, BY THE DEFIBRILLATOR, A REPRESENTATION OF AN ECG SIGNAL OBTAINED USING THE ECG ELECTRODE CABLE IN THE PRIMARY CHANNEL — 1008

FIG. 10

AUTOMATIC LEAD SWITCHING

CROSS-REFERENCE TO RELATED APPLICATIONS

The present application claims priority to U.S. provisional application No. 63/121,107, filed on Dec. 3, 2020, the entire contents of which are herein incorporated by reference.

BACKGROUND

During a cardiac arrest, a defibrillator can provide potentially lifesaving defibrillation treatment. For instance, the defibrillator can be configured to supply a charge through the patient's heart via a set of therapy pads of a therapy cable. The therapy pads are located at a first end of the therapy cable and applied to chest of a patient. At a second end of the therapy cable, a connector couples the therapy cable to a therapy cable receptacle. The therapy cable receptacle is, in turn, coupled to an electrical source of the defibrillator that is configured to generate a shock.

The therapy pads can also include electrodes that the defibrillator can use to measure electrical activity of a patient's heart. In operation, the defibrillator may use the electrodes of the therapy pads to measure voltage, and output one or more graphs of voltage over time, referred to as an electrocardiogram (ECG). A medical professional can evaluate an ECG to diagnose a patient's condition.

Further, some defibrillators include an ECG cable receptacle that is configured to receive an ECG electrode cable. The ECG electrode cable can include multiple electrodes that can be applied to a patient's skin. In addition to or as an alternative to using the electrodes of the therapy pads, the defibrillator can use the electrodes of the ECG electrode cable to measure electrical activity of the patient's heart.

An ECG lead is a view of electrical activity of a heart from a particular angle. A defibrillator can use therapy pads to obtain an ECG lead, commonly referred to as a pads lead. Additionally or alternatively, a defibrillator can use electrodes of an ECG electrode cable to obtain one or multiple ECG leads.

SUMMARY

Within examples described herein, systems and methods are described that include causing a defibrillator to automatically change a source of a displayed ECG waveform to a different source based on which electrodes an operator has connected to a patient.

The features, functions, and advantages that have been discussed can be achieved independently in various examples or may be combined in yet other examples. Further details of the examples can be seen with reference to the following description and drawings.

BRIEF DESCRIPTION OF THE FIGURES

The novel features believed characteristic of the illustrative examples are set forth in the appended claims. The illustrative examples, however, as well as a preferred mode of use, further objectives and descriptions thereof, will best be understood by reference to the following detailed description of an illustrative example of the present disclosure when read in conjunction with the accompanying drawings, wherein:

FIG. 10 shows a flowchart of an example of a method performed by a defibrillator, according to an example implementation.

DETAILED DESCRIPTION

Figure 1:
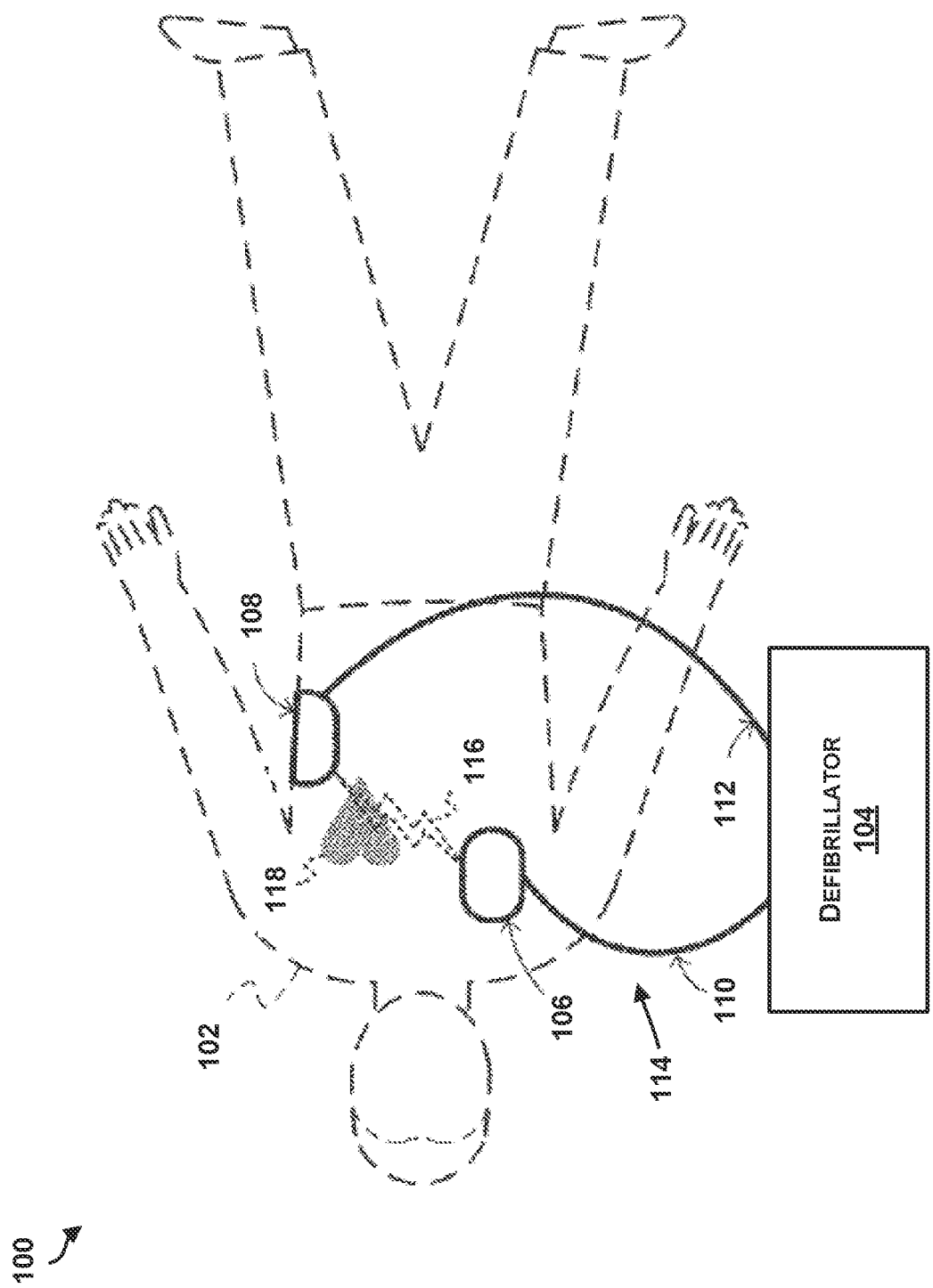
FIG. 1 illustrates an example defibrillation scene showing use of a defibrillator, according to an example implementation.

Disclosed examples will now be described more fully hereinafter with reference to the accompanying drawings, in which some, but not all of the disclosed examples are shown. Indeed, several different examples may be described and should not be construed as limited to the examples set forth herein. Rather, these examples are described so that this disclosure will be thorough and complete and will fully convey the scope of the disclosure to those skilled in the art.

When a user is operating a defibrillator to provide care to a patient, a user interface of the defibrillator can display physiological monitoring data. The physiological monitoring data can include one more waveforms. For instance, the physiological monitoring data can include one or more ECG waveforms as well as waveforms indicative of other patient physiological monitoring data (e.g., a plethysmograph, a capnography waveform, etc.) The physiological monitoring data can also include numerical values, such as a heart rate, respiration rate, or body temperature. The user interface can include a primary channel for displaying a primary waveform, and one or more secondary channels for displaying secondary data, such as secondary waveforms and/or numerical values. The primary channel can be provided near the top of a content area on a user interface screen, and the one or more secondary channels can be provided beneath the primary channel.

In some instances, after powering on a defibrillator, it can be challenging for infrequent users of a defibrillator or users in a stressful situation to obtain a valid ECG waveform from a particular source (e.g., a therapy cable or an ECG electrode cable). For instance, current defibrillators provide a user configurable setup option that allows for configuring which ECG waveform is displayed in a primary channel by default when powering on the defibrillator. The configured ECG waveform is then displayed at power up and remains displayed in the primary channel unless manually changed by the user via the user interface or other controls of the defibrillator.

As an example, if a pads lead obtained using therapy pads of a therapy cable is configured as a default ECG waveform, the pads lead is displayed at power up in a primary channel, and remains displayed in the primary channel until the user adjusts settings of the user interface. This approach may be suitable if the user has connected therapy electrodes to a patient. If, however, the user has not connected therapy pads of a therapy cable to the patient and has instead connected electrodes of an ECG electrode cable to the patient, it can be challenging for the user to quickly reconfigure the user interface such that the user interface of the defibrillator displays an ECG lead obtained using the ECG electrode cable in the primary channel.

Example methods and systems describe a defibrillator that automatically changes a source of a displayed ECG waveform to a different source based on an ECG source an operator has connected to a patient. For instance, as described herein, a defibrillator can, by default, display an ECG waveform obtained using therapy pads of a therapy cable when the defibrillator is powered on. The rationale for this configuration is that, for a patient needing defibrillation, the operator of the defibrillator will be connecting therapy pads to the patient. Accordingly, displaying the pads lead obtained using the therapy pads without the operator having to adjust the user interface is beneficial.

At or after power on, if the defibrillator detects a patient connection for an ECG lead of an ECG electrode cable prior to detection of a patient connection for the pads lead, the defibrillator can cause the user interface to switch from displaying the pads lead to displaying the ECG lead obtained using the ECG electrode cable. For instance, the defibrillator can cause a primary channel to switch from displaying the pads lead to displaying an ECG lead. As such, the methods and systems help eliminate the need for the operator to interact with user-interface controls of the defibrillator to display a valid ECG waveform.

Alternatively, a defibrillator can, by default, display an ECG waveform for an ECG lead of an ECG electrode cable when the defibrillator is powered on. At or after power on, if the defibrillator detects a patient connection for a pads lead prior to detection of a patient connection for the ECG lead, the defibrillator can cause the user interface to switch from displaying the ECG lead to displaying the pads lead. For instance, the defibrillator can cause a primary channel to switch from displaying an ECG lead to displaying a pads lead.

Further details and features of these methods and systems are described hereinafter with reference to the figures.

Referring now to the figures, FIG. 1 illustrates an example defibrillation scene 100 showing use of a defibrillator. As shown in FIG. 1, a patient 102 is lying on their back. The patient 102 could be a patient in a public space, a home, a pre-hospital environment, or even a hospital. A defibrillator 104 is currently being used to treat the patient 102. As shown in FIG. 1, therapy pads 106, 108 of the defibrillator 104 are applied to a chest of the patient 102. The therapy pad 106 is coupled to the defibrillator 104 via a lead wire 110. The therapy pad 108 is coupled to the defibrillator 104 via a lead wire 112. The therapy pads 106, 108 and the lead wires 110, 112 are collectively referred to as a therapy cable 114. The defibrillator 104 can be used to deliver, via therapy cable 114, a shock 116. The shock 116 can go through a heart 118 of the patient 102, in an attempt to restart the heart 118, for saving the life of the patient 102.

Figure 2:
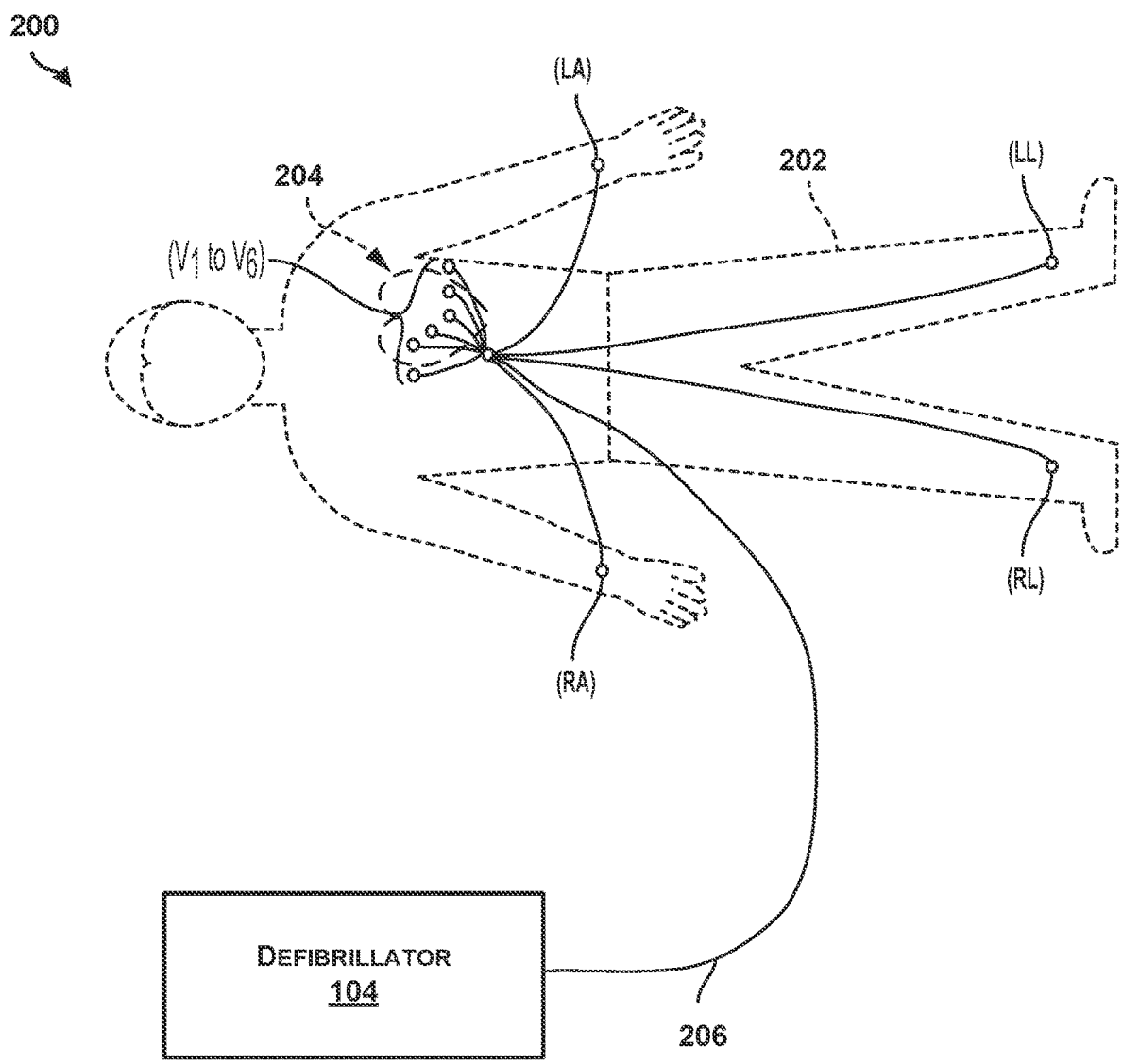
FIG. 2 illustrates another example defibrillation scene showing use of the defibrillator of FIG. 1, according to an example implementation.

FIG. 2 illustrates another example defibrillation scene 200 showing use of the defibrillator 104 of FIG. 1. As shown in FIG. 2, a patient 202 is lying on their back. The patient 202 may be experiencing a condition in their heart 204, or they may be experiencing a different medical problem such as stroke. The defibrillator 104 has been brought close to the patient 202. The defibrillator 104 receives voltage signals from multiple electrodes through ECG electrode cable 206, and the defibrillator 104 combines the voltage signals in various ways to form multiple ECG leads.

In FIG. 2, the multiple electrodes include ten electrodes. The ten electrodes include four limb electrodes: RA (right arm), LA (left arm), RL (right leg), and LL (left leg); and six precordial (chest) electrodes, which are labeled $V_1$ to $V_6$ (precordial electrodes). Each of the ten electrodes may be coupled to the patient 202 using adhesive and are typically about two inches in diameter, for example.

In FIG. 2, a 12-lead ECG system is shown in which the ten electrodes provide twelve perspectives of activity of the heart 204 using different angles through two electrical planes, namely, frontal and horizontal planes. The twelve ECG leads include: three bipolar limb leads (I, II, and III), three augmented limb leads (augmented vector right (aVR), augmented vector left (aVL), and augmented vector foot (aVF)), and six chest leads also called precordial or V leads, (V1, V2, V3, V4, V5, and V6). In this document, precordial electrodes and lead wires will use subscripted numbers in their labels (e.g., $V_1$) and precordial leads will not (e.g., V1).

By using three limb electrodes (RA, LA, and LL), six frontal leads can be derived that provide information about the vertical plane of the heart 204. The six frontal leads can be labeled and derived using the lead equations shown below. The RL electrode is the neutral electrode and is not used in any lead equations.

$$I = LA - RA \qquad \text{Equation (1)}$$

$$II = LL - RA \qquad \text{Equation (2)}$$

$$III = LL - LA \qquad \text{Equation (3)}$$

$$aVR = RA - (LA + LL)/2 \qquad \text{Equation (4)}$$

$$aVL = LA - (RA + LL)/2 \qquad \text{Equation (5)}$$

$$aVF = LL - (LA + RA)/2 \qquad \text{Equation (6)}$$

Limb lead I is taken between a negative electrode placed on the right arm and a positive electrode placed on the left arm; limb lead II between a negative electrode placed on the right arm and a positive electrode placed on the left leg; and so forth. These and the other electrode pairings to form the 12-lead ECG orientations are well known in electrocardiography.

Then, by using the six chest electrodes, six precordial leads can be derived that provide information about the horizontal plane of the heart 204 using the lead equations shown below.

$$V1 = V_1 - (LA + RA + LL)/3 \qquad \text{Equation (7)}$$

$$V2 = V_2 - (LA + RA + LL)/3 \qquad \text{Equation (8)}$$

$$V3 = V_3 - (LA + RA + LL)/3 \qquad \text{Equation (9)}$$

$$V4 = V_4 - (LA + RA + LL)/3 \qquad \text{Equation (10)}$$

$$V5 = V_5 - (LA + RA + LL)/3 \qquad \text{Equation (11)}$$

$$V6 = V_6 - (LA + RA + LL)/3 \qquad \text{Equation (12)}$$

In other examples, the ECG electrode cable 206 can include a greater or lesser number of lead wires and electrodes, and can be used to obtain a different number of ECG leads. For instance, the ECG electrode cable 206 can be a 3-wire cable assembly that provides three ECG leads, a 4-wire cable assembly that provides six ECG leads, a 5-wire cable assembly that provides seven ECG leads, or a 13-wire cable assembly that provides fifteen ECG leads.

The defibrillator 104 can be one of multiple different types, each with different sets of features and capabilities. As one example, the defibrillator 104 can be an AED, such as a public access defibrillator AED. An AED can make a decision as to whether or not to deliver a shock to a patient automatically. For example, an AED can sense physiological conditions, such as shockable heart rhythms, of a patient via therapy pads applied to the patient, and make the decision based on an analysis of the patient's heart. Further, an AED can either deliver the shock automatically, or instruct a user to deliver a shock, e.g., by pushing a button. AEDs can be operated by medical professionals as well as people who are not in the medical profession, such as policemen, firemen, or even a person with first-aid and CPR/AED training. AEDs can be located in public spaces or homes so that lifesaving treatment can hopefully be initiated before medical professionals arrive.

As another example, the defibrillator 104 can be a more advanced device, such as a monitor defibrillator. Monitor defibrillators are intended to be used by trained medical professionals, such as doctors, nurses, paramedics, emergency medical technicians, etc. As the name suggests, a monitor defibrillator is a combination of a monitor and a defibrillator. As a defibrillator, a monitor defibrillator can be one of different varieties, or even versatile enough to be able to switch among different modes that individually correspond to the varieties. One variety is that of an automated defibrillator, which can determine whether a shock is needed and, if so, charge to a predetermined energy level and instruct the user to deliver the shock. Another variety is that of a manual defibrillator, where the user determines the need and controls delivery of the shock. As a patient monitor, the monitor defibrillator has features additional to what is needed for operation as a defibrillator. These features can be for monitoring physiological indicators of a patient in an emergency scenario, for instance.

Figure 3:
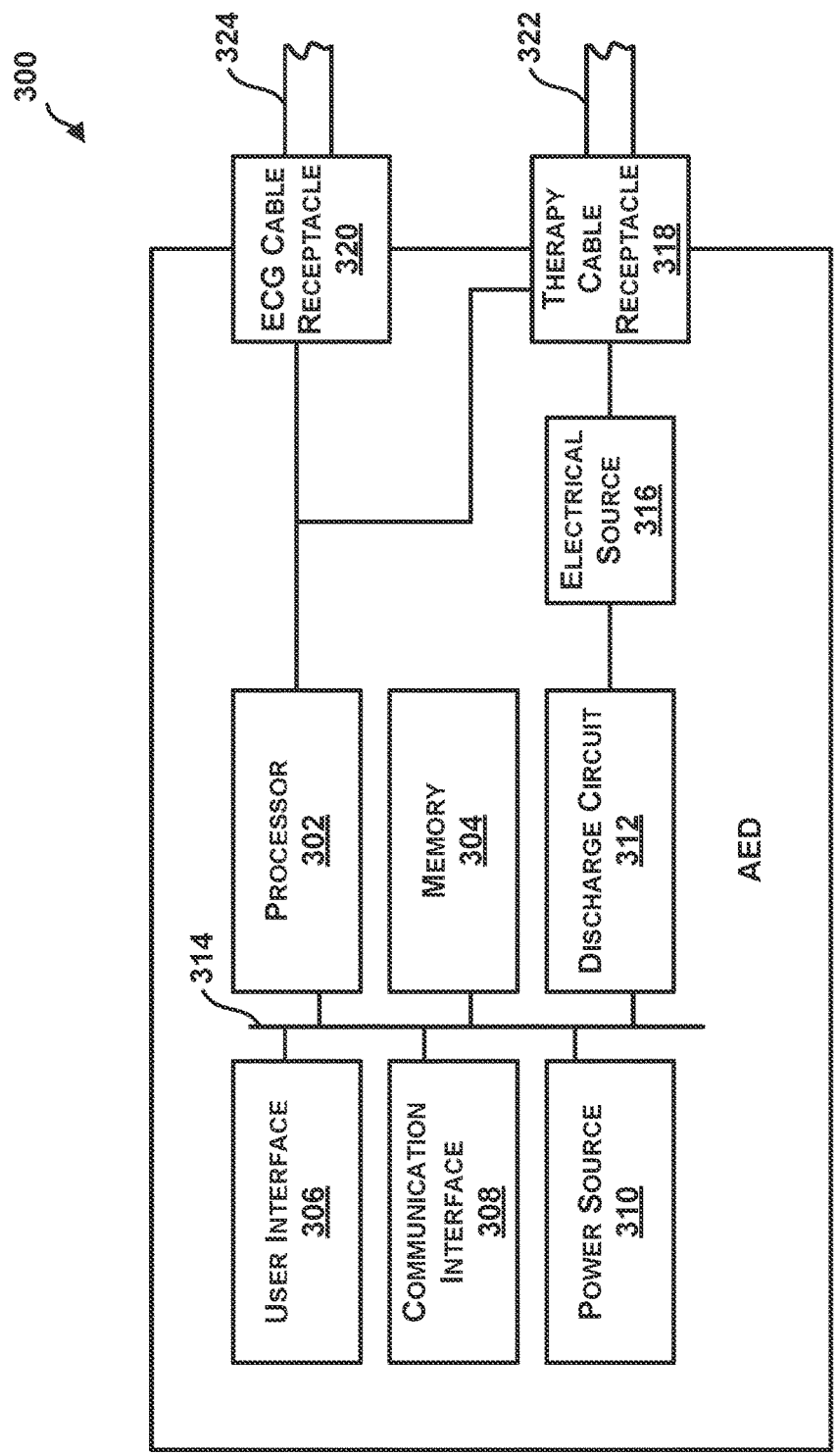
FIG. 3 is a block diagram of an example defibrillator, according to an example implementation.

FIG. 3 illustrates an example AED 300. In FIG. 3, the AED 300 includes a processor 302, a memory 304, a user interface 306, a communication interface 308, a power source 310, and a discharge circuit 312, each connected to a communication bus 314. The AED 300 also includes an electrical source 316 connected to discharge circuit 312, and a therapy cable receptacle 318 connected to the electrical source 316. Further, the AED 300 includes an ECG cable receptacle 320.

Memory 304 may include one or more computer-readable storage media that can be read or accessed by processor 302. The computer-readable storage media can include volatile and/or non-volatile storage components, such as optical, magnetic, organic or other memory or disc storage, which can be integrated in whole or in part with processor 302. The non-transitory data storage is considered non-transitory computer readable media. In some examples, the non-transitory data storage can be implemented using a single physical device (e.g., one optical, magnetic, organic or other memory or disc storage unit), while in other examples, the non-transitory data storage can be implemented using two or more physical devices.

The non-transitory data storage thus is a computer readable medium, and instructions are stored thereon. The instructions include computer executable code.

The processor 302 may be a general-purpose processor or a special purpose processor (e.g., digital signal processor, application specific integrated circuit, etc.). The processor 302 may receive inputs from other components of the AED 300 and process the inputs to generate outputs that are stored in the non-transitory data storage. The processor 302 can be configured to execute instructions (e.g., computer-readable program instructions) that are stored in the non-transitory data storage and are executable to provide the functionality of the AED described herein. For example, the processor 302 can execute instructions for detecting a lack of a patient connection for therapy pads of a therapy cable 322, and detecting a patient connection for an ECG lead that is obtained using an ECG electrode cable 324. The processor 302 can also execute instructions for causing the AED 300 to display an ECG waveform obtained using the ECG electrode cable 324 in a primary channel of a user interface screen based on detecting a lack of a patient connection for the therapy pads and detecting a patient connection for the ECG lead obtained using the ECG electrode cable 324.

The user interface 306 can take any of a number of forms. For example, the user interface 306 may include output devices, which can be visual, audible or tactile, for communicating to a user. An output device can be configured to output a warning, which warns or instructs the patient or a bystander to do something. An output device can be a light or a screen to display what is detected and measured, and provide visual feedback to the rescuer for their resuscitation attempts. The user interface 306 may also include a speaker, to issue voice prompts or sounds. The user interface 306 may additionally include input devices for receiving inputs from users. Such input devices may include various controls, such as pushbuttons, keyboards, touchscreens, or a microphone.

The communication interface 308 may be one or more wireless interfaces and/or one or more wireline interfaces that allow for both short-range communication and long-range communication to one or more networks or to one or more remote devices. Such wireless interfaces may provide for communication under one or more wireless communication protocols, such as Bluetooth, Wi-Fi (e.g., an institute of electrical and electronic engineers (IEEE) 802.11 protocol), Long-Term Evolution (LTE), cellular communications, near-field communication (NFC), and/or other wireless communication protocols. Such wireline interfaces may include an Ethernet interface, a Universal Serial Bus (USB) interface, or similar interface to communicate via a wire, a twisted pair of wires, a coaxial cable, an optical link, a fiber-optic link, or other physical connection to a wireline network. The communication interface 308 thus may include hardware to enable communication between the AED 300 and other devices (not shown). The hardware may include transmitters, receivers, and antennas, for example.

The power source 310 may include battery power, or a wired power means such as an AC power connection.

The electrical source 316 can be configured to store electrical energy in the form of an electrical charge, when preparing for delivery of a shock. The discharge circuit 312 can be controlled to permit the energy stored in electrical source 316 to be discharged to therapy pads of the therapy cable 322. The discharge circuit 312 can include one or more switches, such as an H-bridge. The processor 302 can instruct the discharge circuit 312 to output a shock using one of various energy levels. The energy levels can range from 1 Joule to 360 Joules. For instance, for an adult, the processor 302 can select an energy level from an adult energy sequence that includes energy levels of 200 Joules, 300 Joules, and 360 Joules. Whereas, for a pediatric patient, the processor 302 can select an energy level from a pediatric energy sequence that includes energy levels of 50 Joules, 75 Joules, and 90 Joules. Alternatively, the processor 302 can select lower energies for use in internal defibrillation or for defibrillation of infant patients.

The therapy cable 322 can be detachable from a housing of the AED 300 by way of a connector of the therapy cable 322 and the therapy cable receptacle 318. For instance, the connector can be a tabbed, male connector that is compatible with the therapy cable receptacle 318. The therapy cable 322 can also include therapy pads, such as the therapy pads 106, 108 of FIG. 1. The therapy pads include sensors (e.g., electrodes) that measure heart electrical activity. In some instances, the therapy pads can be used to measure a heart rate.

The ECG electrode cable 324 can be detachable from the housing of the AED 300 by way of a connector of the ECG electrode cable 324 and the ECG cable receptacle 320. For instance, the connector can be a tabbed, male connector that is compatible with the ECG cable receptacle 320. The ECG electrode cable can also include ECG electrodes, such as those described above with reference to FIG. 1. In some instances, the ECG electrode cables can be used to measure a heart rate.

In some examples, the AED 300 can include filtering hardware (e.g., amplifiers, filters, etc.) configured to filter analog ECG signals before the ECG signals are digitized and then further processed/filtered by the processor 302.

Figure 4:
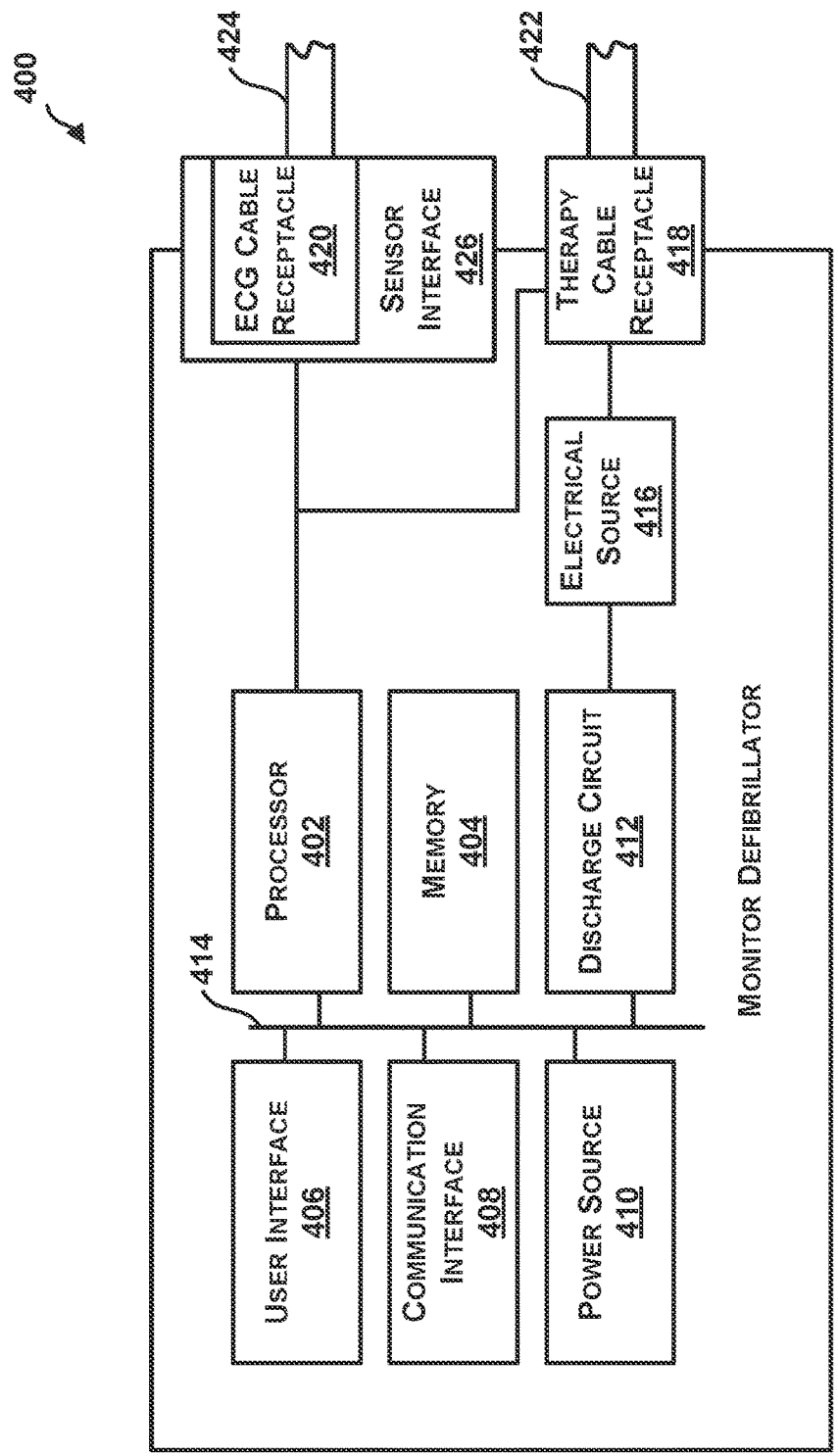
FIG. 4 is a block diagram of another example defibrillator, according to an example implementation.

FIG. 4 illustrates an example monitor defibrillator 400. Like the AED 300 of FIG. 3, the monitor defibrillator 400 includes a processor 402, a memory 404, a user interface 406, a communication interface 408, a power source 410, and a discharge circuit 412, each connected to a communication bus 414. The monitor defibrillator 400 also includes an electrical source 416 connected to a discharge circuit 412, and a therapy cable receptacle 418 connected to the electrical source 416. Further, the monitor defibrillator 400 includes an ECG cable receptacle 420. Still further, the monitor defibrillator 400 can include filtering hardware (e.g., amplifiers, filters, etc.) configured to filter analog ECG signals before the ECG signals are digitized and then further processed/filtered by the processor 402.

Unlike the AED 300, the monitor defibrillator 400 includes a sensor interface 426 that is configured to couple physiologic monitoring sensors with processor 402. Physiologic monitoring sensors allow for monitoring physiological indicators of a patient. As shown in FIG. 4, the sensor interface 426 includes the ECG cable receptacle 420. However, any number or type of sensors may be used depending on treatment or monitoring of the patient. In many instances, a variety of sensors are used to determine a variety of physiologic monitoring data.

Physiologic monitoring data can include vital sign data (e.g., heart rate, respiration rate, blood pressure, and body temperature), as well as signals from other sensors described herein. In addition, physiologic monitoring data can also include treatment monitoring data, such as location at which an endotracheal tube has been placed or other sensor context information. The physiologic monitoring data can include timestamps associated with a time of collection and may be considered a measurement at a specific time. In some instances herein, physiologic monitoring data refers to one measurement and data associated with the one measurement, and in other instances, physiologic monitoring data refers to a collection of measurements as context indicates.

In some instances, the sensor interface 426 includes one or more physiologic monitoring sensors. Additionally or alternatively, the sensor interface 426 can include receptacles for connecting removable physiologic monitoring sensors to the monitor defibrillator 400.

Physiologic monitoring sensors can include sensors that measure heart electrical activity such as electrocardiogram (ECG), saturation of the hemoglobin in arterial blood with oxygen (SpO2), carbon monoxide (carboxyhemoglobin, COHb) and/or methemoglobin (SpMet), partial pressure of carbon dioxide (CO2) in gases in the airway by means of capnography, total air pressure in the airway, flow rate or volume of air moving in and out of the airway, blood flow, blood pressure such as non-invasive blood pressure (NIBP) or invasive blood pressure (IP) by means of a catheter, core body temperature with a temperature probe in the esophagus, oxygenation of hemoglobin within a volume of tissue (rSO2), indicating level of tissue perfusion with blood and supply of oxygen provided by that perfusion, and so forth.

Outputs, e.g., signals, from physiologic monitoring sensors are conveyed to the processor 402 by way of the sensor interface 426. The processor 402 records the signals and uses the signals for vital sign qualification and caregiver feedback. In some examples, outputs from physiologic monitoring sensors or data derived from an analysis of the outputs can be recorded in a patient care record of monitor defibrillator 400 and delivered to subsequent entities (e.g., hospital emergency department, etc.) via the communication interface 408.

Within one example, the memory 404 can store instructions that are executable by the processor 402 to perform a set of acts including detecting a lack of a patient connection for therapy pads of a therapy cable 422, and detecting a patient connection for an ECG lead that is obtained using an ECG electrode cable 424. The set of acts can also include causing the monitor defibrillator 400 to display an ECG waveform obtained using the ECG electrode cable 424 in a primary channel of a user interface screen based on detecting a lack of a patient connection for therapy pads and detecting a patient connection for an ECG lead obtained using the ECG electrode cable 424.

Figure 5:
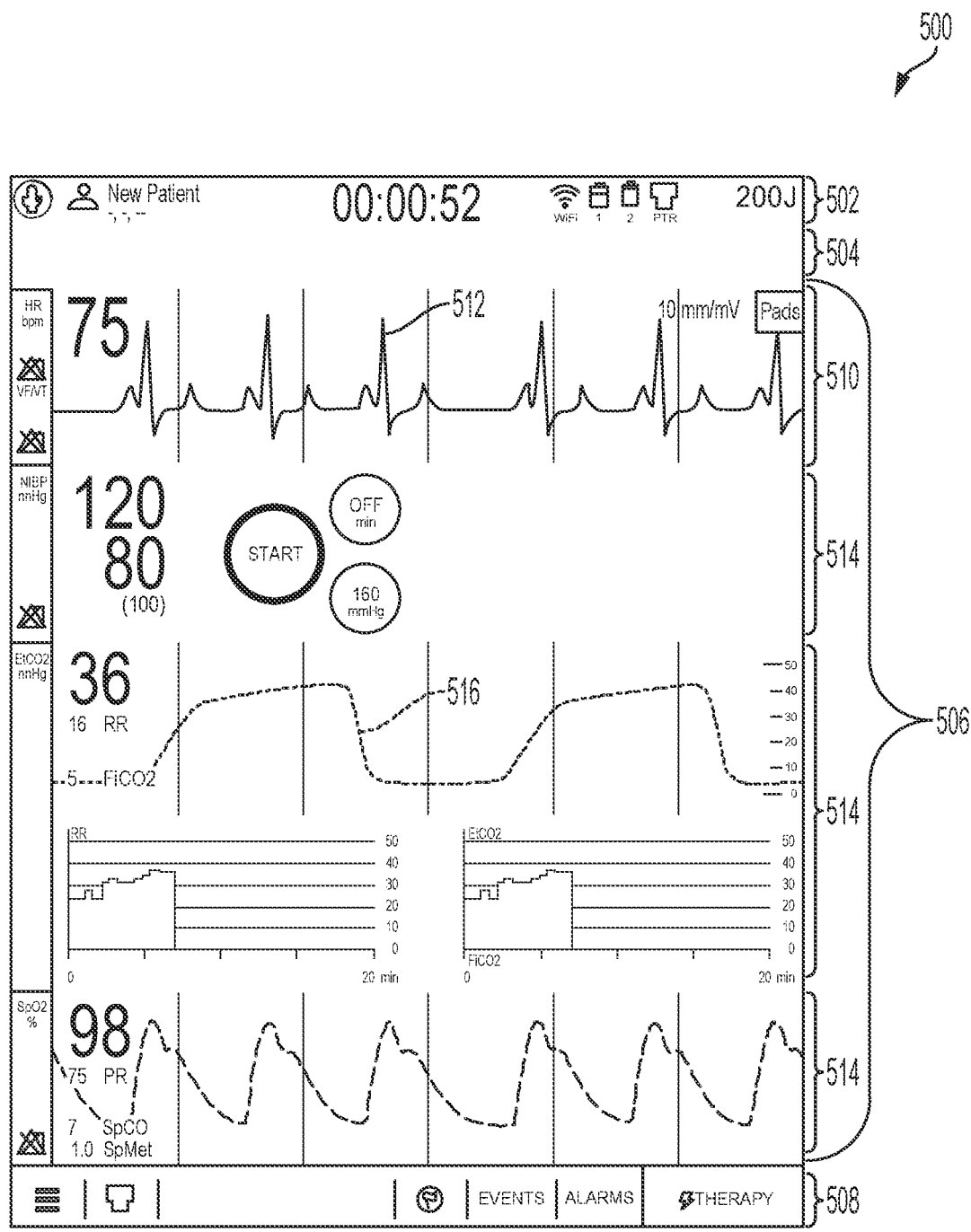
FIG. 5 is an example user interface screen, according to an example implementation.

FIG. 5 is an example user interface screen 500. The user interface screen 500 can be displayed by a defibrillator, such as defibrillator 104 of FIGS. 1 and 2, the AED 300 of FIG. 3, or the monitor defibrillator 400 of FIG. 4. As shown in FIG. 5, the user interface screen 500 includes a status bar 502, a messaging area 504, a content area 506, and a navigation bar 508.

The content area 506 includes multiple channels, including a primary channel 510 for displaying a primary waveform 512 and multiple secondary channels 514 for displaying secondary data, such as a secondary waveform 516. The primary channel 510 is positioned above the secondary channels 514. Although multiple secondary channels 514 are shown, in other examples, a user interface screen might only display a single secondary channel.

In FIG. 5, the primary waveform 512 is shown as an ECG waveform, namely, a pads lead obtained using therapy pads of a therapy cable. In some examples, the secondary channels 514 can also display one or more ECG waveforms (not shown in FIG. 5).

Figure 6:
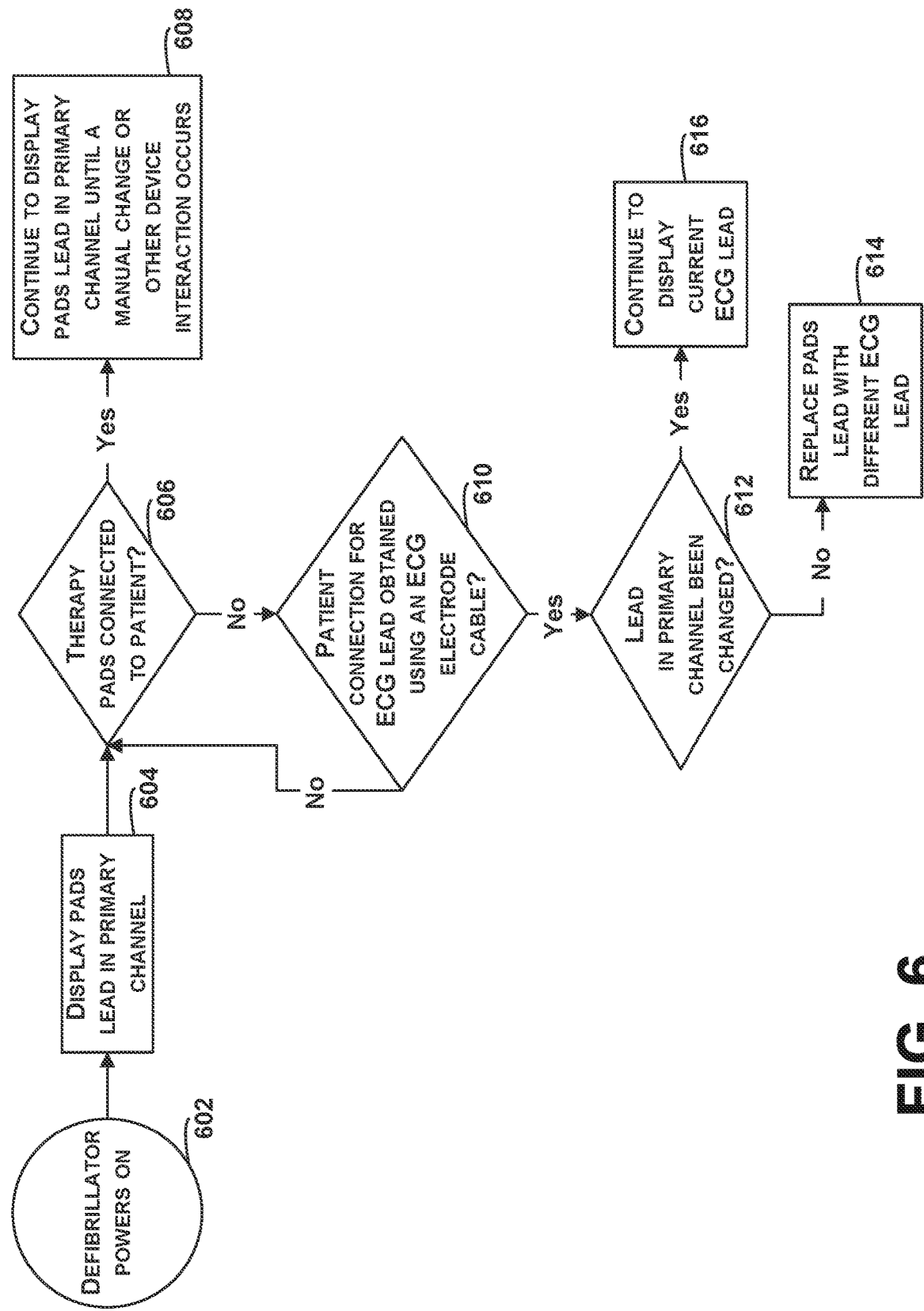
FIG. 6 is a block diagram illustrating example acts that can be carried out in conjunction with use of a defibrillator, according to an example implementation.

In line with the discussion above, a defibrillator can, by default, display an ECG waveform obtained using therapy pads of a therapy cable when the defibrillator is powered on. Further, at or after power on, if the defibrillator detects a patient connection for an ECG lead of an ECG electrode cable prior to detection of a patient connection for the pads lead, the defibrillator can cause the user interface to switch from displaying the pads lead to displaying the ECG lead obtained using the ECG electrode cable. FIG. 6 is a block diagram illustrating a set of acts that can be carried out in conjunction with use of a defibrillator.

As shown in FIG. 6, at block 602, the defibrillator powers on. Subsequently, at block 604, the defibrillator displays a placeholder for a pads lead obtained using a therapy cable in a primary channel of a user interface screen. The placeholder can include a lead label and a dashed line.

Further, at block 606, the defibrillator determines whether or not therapy pads are connected to a patient. The defibrillator can determine whether or not therapy pads are connected to a patient by measuring a patient impedance. For instance, the defibrillator can use an AC current at 20 kHz to measure an impedance between a first therapy pad and a second therapy pad. If a resistive part of the impedance is greater than a first threshold (e.g., 300 ohms) or a magnitude of the patient is greater than a second threshold (e.g., 440 ohms), the defibrillator can determine that one or both of the therapy pads are not connected to the patient. Whereas, if the resistive part of the impedance is less than or equal to the first threshold and the magnitude of the impedance is less than or equal to the second threshold, the defibrillator can determine that the therapy pads are connected to the patient. Alternatively, the defibrillator can measure patient impedance using a DC current.

Further, as shown in FIG. 6, at block 608, upon determining that the therapy pads are connected to the patient, the defibrillator can continue to display the pads lead in the primary channel until a manual change or other device interaction occurs. For instance, the defibrillator can continue to display the pads lead in the primary channel until a user manually changes the waveform to be displayed in the primary channel using the user interface, or the user enters a different mode of the defibrillator using the user interface. Whereas, upon determining that the therapy pads are not connected to the patient, at block 610, the defibrillator determines whether or not there is a patient connection for an ECG lead that is obtained using an ECG electrode cable.

In some examples, determining whether or not there is a patient connection for an ECG lead that is obtained using an ECG electrode cable can involve determining whether or not that there is a patient connection for any ECG lead that is obtained using an ECG electrode cable. Alternatively, in other examples, determining whether or not there is a patient connection for an ECG lead that is obtained using an ECG electrode cable can involve determining whether or not there is a patient connection for any bipolar limb leads. In still other examples, determining whether or not there is a patient connection for an ECG lead that is obtained using an ECG electrode cable can involve determining whether or not there is a patient connection for a particular ECG lead that is obtained using an ECG electrode cable (e.g., bipolar limb lead II).

The defibrillator can determine whether or not there is a patient connection for an ECG lead that is obtained using an ECG electrode cable by determining whether or not each of multiple electrodes used to develop such an ECG lead are connected to the patient. Based on determining that each of multiple electrodes used to develop the ECG lead are connected to the patient, the defibrillator can determine that there is a patient connection for the ECG lead. Conversely, based on determining that one or more of the electrodes used to develop the ECG lead are not connected to the patient, the defibrillator can determine that there is not a patient connection for the ECG lead. For instance, to determine whether there is a patient connection for bipolar limb lead II, the defibrillator can determine whether each of the RA, LA, and LL limb electrodes are connected to the patient. If the defibrillator determines that each of the RA, LA, and LL limb electrodes are connected to the patient, the defibrillator can interpret that determination to mean that there is a patient connection for bipolar limb lead II. Conversely, if the defibrillator determines that one of the RA, LA, and LL limb electrodes are not connected to the patient, the defibrillator can interpret that determination to mean that there is not a patient connection for bipolar limb lead II.

The defibrillator can determine whether particular electrodes are connected to the patient by measuring patient impedance between pairs of electrodes. As an example, the defibrillator can use a DC current and a common mode drive signal to measure an impedance between a first electrode and a second electrode. If the impedance satisfies a threshold condition, the defibrillator can determine that the first electrode and the second electrode are connected to the patient. Whereas, if the impedance does not satisfy a threshold condition, the defibrillator can determine that either the first electrode or the second electrode are not connected to the patient. By repeating this process for different pairs of electrodes, the defibrillator can determine which electrodes are connected to a patient and which electrodes are not connected to a patient. Alternatively, the defibrillator can measure patient impedance using an AC current.

Upon determining that there is not a patient connection for an ECG lead that is obtained using an ECG electrode cable, the defibrillator can again determine or whether or not the therapy pads are connected to the patient. Whereas, upon determining that there is a patient connection for an ECG lead that is obtained using an ECG electrode cable, at block 612, the defibrillator can then determine whether or not the lead displayed in the primary channel has been changed since the defibrillator has been powered on.

The defibrillator can determine whether or not the lead displayed in the primary channel has been changed in various ways. As one example, the defibrillator can determine whether or not the pads lead is currently displayed in the primary channel. If the pads lead is not currently displayed in the primary channel, the defibrillator can interpret this determination to mean that the lead displayed in the primary channel has already been changed since the defibrillator has been powered on.

As another example, the defibrillator can be configured to store change data in a memory any time a user changes the lead in the primary channel. For instance, upon detecting that a user changes the lead in the primary channel from the pads lead to a different lead, the defibrillator can update a change-occurred flag to indicate that a change has occurred. With this approach, the defibrillator can determine whether or not the lead displayed in the primary channel has been changed by accessing and interpreting the change-occurred flag. One advantage of this approach is that if the lead displayed in the primary channel was manually changed from a pads lead to a different lead and then manually changed back to the pads lead, the change data stored in the memory would be updated such that the defibrillator can correctly determine that the lead in the primary channel has been changed even though the pads lead is currently displayed.

As shown in FIG. 6, at block 614, based on determining that the lead displayed in the primary channel has not been changed since the defibrillator has been powered on, the defibrillator can replace the pads lead with a different ECG lead that is obtained using the ECG electrode cable. For instance, the defibrillator can replace the pads lead with a default ECG lead that is obtained using the ECG electrode cable, such as bipolar limb lead II. In some instances, replacing the pads lead with a different ECG lead that is obtained using the ECG electrode cable can involve displaying the pads lead in a secondary channel.

As further shown in FIG. 6, at block 616, based on determining that the lead displayed in the primary channel has already been changed since the defibrillator has been powered on, the defibrillator can continue to display the current ECG lead. In this manner, if the defibrillator has already replaced the pads lead with an ECG lead obtained using the ECG electrode cable, the defibrillator can continue to display the ECG lead obtained using the ECG electrode cable. Similarly, if the user switched from the pads lead to an ECG lead, and then switched back to the pads lead, the defibrillator can continue to display the pads lead.

In some examples, the switching of the waveform displayed in the primary channel is further based on physiologic monitoring data obtained using a sensor of the defibrillator. For instance, after determining, at block 612, that the lead displayed in the primary channel has not been changed since the defibrillator has been powered on, and making a determination that physiologic monitoring data obtained using a sensor of the defibrillator satisfies a threshold condition, the defibrillator can then can replace the pads lead with a different ECG lead that is obtained using the ECG electrode cable.

The set of acts illustrated by the block diagram of FIG. 6 relate to a configuration in which, by default, the defibrillator displays an ECG waveform obtained using therapy pads of a therapy cable in a primary channel when the defibrillator is powered on. However, the set of acts are not meant to be limiting. In other examples, a defibrillator can be configured to, by default, display an ECG waveform obtained using an ECG electrode cable in a primary channel when the defibrillator is powered on. Further, at or after power on, if the defibrillator detects a patient connection for a pads lead prior to detection of a patient connection for the ECG lead, the defibrillator can cause the user interface to switch from displaying the ECG lead in the primary channel to displaying the pads lead.

By way of example, an example method can involve: (i) displaying, by a defibrillator, a user interface screen that includes a primary channel for displaying a primary waveform and a secondary channel for displaying secondary data; (ii) detecting, by the defibrillator, a lack of a patient connection for an ECG lead obtained using the ECG electrode cable; (iii) detecting, by the defibrillator, a patient connection for the therapy pads; and (iv) based on detecting the lack of the patient connection for the ECG lead and detecting the patient connection for the therapy pads, displaying a representation of an ECG signal obtained using the therapy pads in the primary channel. One of ordinary skill will appreciate that the defibrillator can perform acts similar to those illustrated by the block diagram of FIG. 6 to carry out this method.

Figure 7:
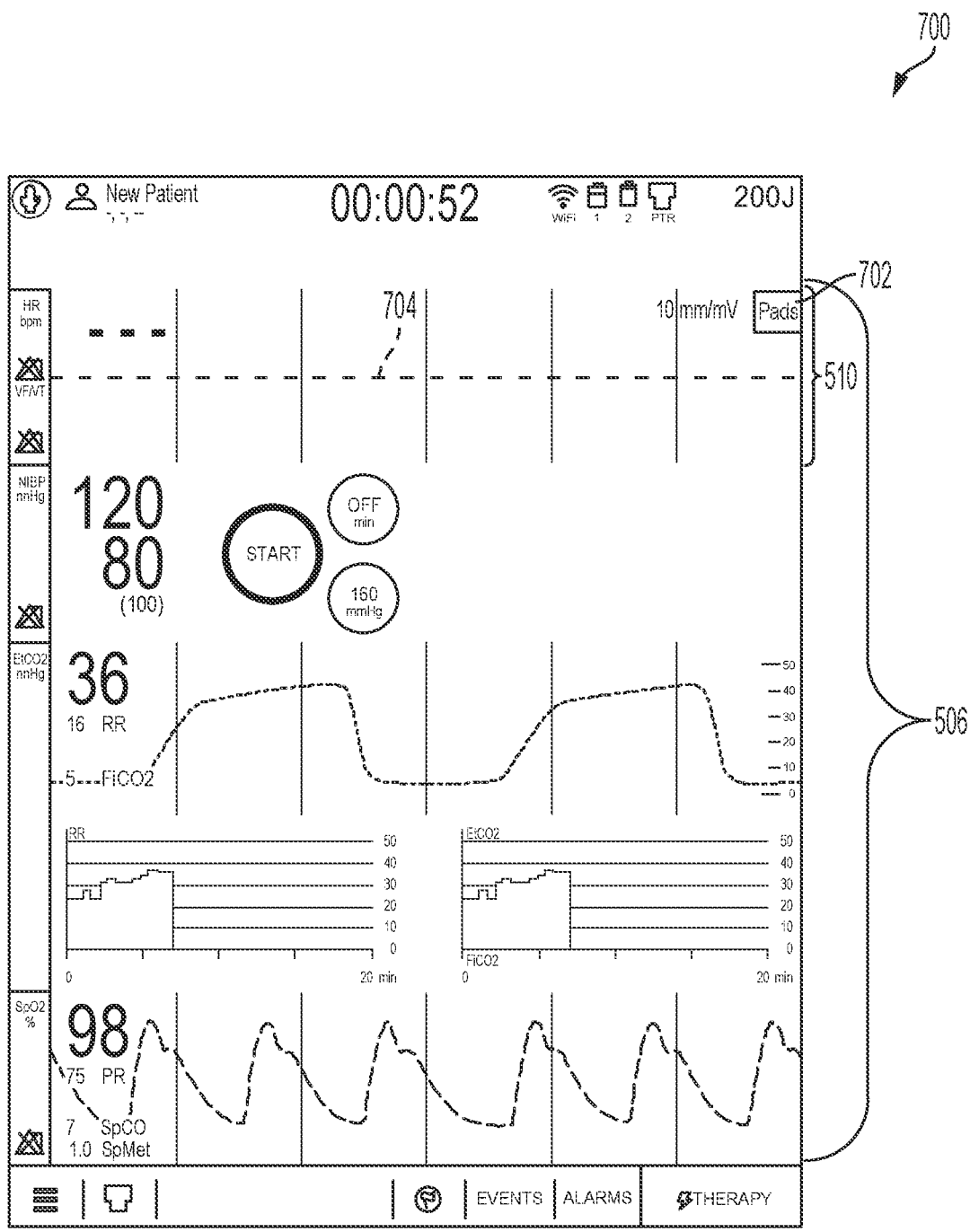
FIG. 7 is another example user interface screen, according to an example implementation.

FIG. 7 is an example user interface screen 700. The user interface screen 700 can be displayed by a defibrillator, such as the defibrillator 104 of FIGS. 1 and 2, the AED 300 of FIG. 3, or the monitor defibrillator 400 of FIG. 4. In particular, the user interface screen 700 can be displayed when a defibrillator is initially powered on and prior to detecting: (i) a lack of a patient connection for therapy pads and (ii) a patient connection for an ECG lead that is obtained using an ECG electrode cable.

As shown in FIG. 7, the user interface screen 700 includes the content area 506. Further, within the primary channel 510 of the content area 506, a placeholder for a pads lead is displayed. The placeholder includes a lead label 702 and a dashed line 704.

Figure 8:
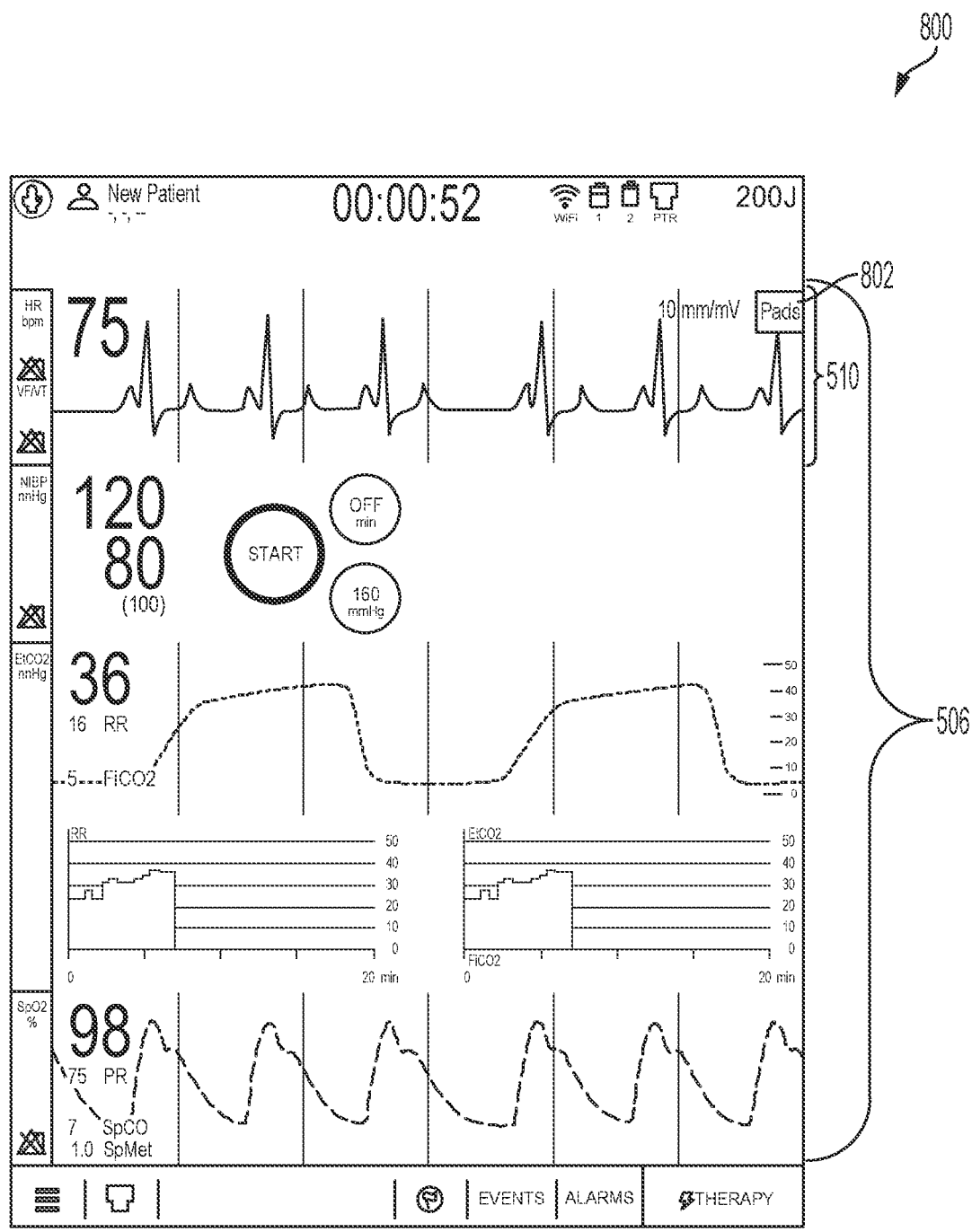
FIG. 8 is another example user interface screen, according to an example implementation.

FIG. 8 is an example user interface screen 800. The user interface screen 800 can be displayed by a defibrillator, such as the defibrillator 104 of FIGS. 1 and 2, the AED 300 of FIG. 3, or the monitor defibrillator 400 of FIG. 4. In particular, the user interface screen 800 can be displayed by the defibrillator based on detecting a patient connection for therapy pads.

As shown in FIG. 8, the user interface screen 800 includes the content area 506. Further, within the primary channel 510 of the content area 506, a pads lead obtained using the therapy pads is displayed. A lead label 802 identifies the pads lead. In some examples, the defibrillator can also display an ECG lead obtained using an ECG electrode cable within a secondary channel of the content area 506 (not shown).

Figure 9:
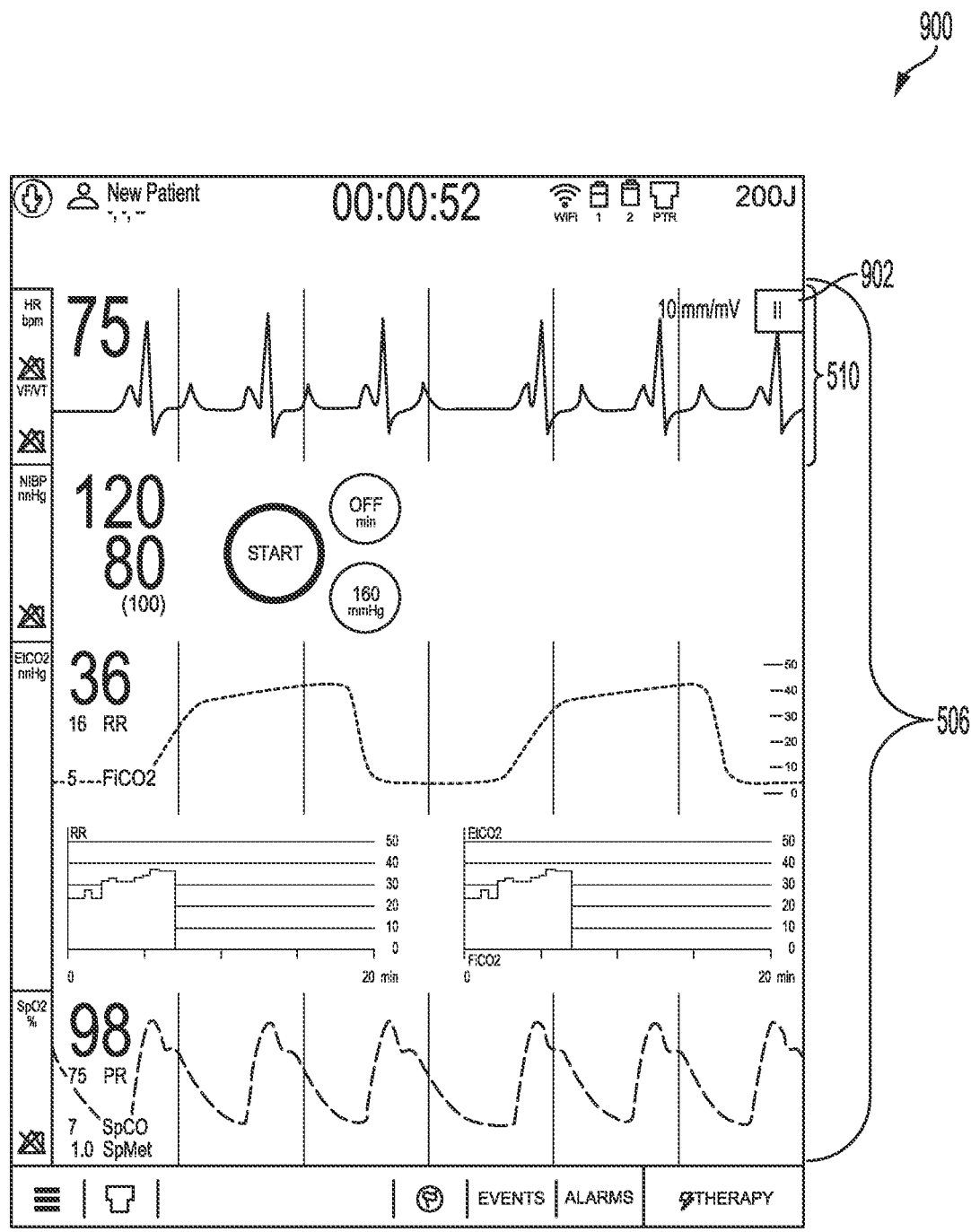
FIG. 9 is another example user interface screen, according to an example implementation.

FIG. 9 is an example user interface screen 900. The user interface screen 900 can be displayed by a defibrillator, such as the defibrillator 104 of FIGS. 1 and 2, the AED 300 of FIG. 3, or the monitor defibrillator 400 of FIG. 4. In particular, the user interface screen 900 can be displayed by the defibrillator based on detecting: (i) a lack of a patient connection for therapy pads and (ii) a patient connection for an ECG lead that is obtained using an ECG electrode cable.

As shown in FIG. 9, the user interface screen 900 includes the content area 506. Further, within the primary channel 510 of the content area 506, an ECG lead obtained using an ECG electrode cable is displayed. In particular, as indicated by a lead label 902, the ECG lead is bipolar limb lead II.

FIG. 10 shows a flowchart of an example of a method 1000. Method 1000 shown in FIG. 10 presents an example of a method that could be performed by a defibrillator, such as the defibrillator 104 of FIGS. 1 and 2, the AED 300 of FIG. 3, or the monitor defibrillator 400 of FIG. 4, for example. Further, devices or systems may be used or configured to perform logical functions presented in FIG. 10. In some instances, components of the devices and/or systems may be configured to perform the functions such that the components are actually configured and structured (with hardware and/or software) to enable such performance. In other examples, components of the devices and/or systems may be arranged to be adapted to, capable of, or suited for performing the functions, such as when operated in a specific manner. Method 1000 may include one or more operations, functions, or actions as illustrated by one or more of blocks 1002-1008. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

It should be understood that for this and other processes and methods disclosed herein, flowcharts show functionality and operation of one possible implementation of present examples. In this regard, each block or portions of each block may represent a module, a segment, or a portion of program code, which includes one or more instructions executable by a processor for implementing specific logical functions or steps in the process. The program code may be stored on any type of computer readable medium or data storage, for example, such as a storage device including a disk or hard drive. Further, the program code can be encoded on a computer-readable storage media in a machine-readable format, or on other non-transitory media or articles of manufacture. The computer readable medium may include non-transitory computer readable medium or memory, for example, such as computer-readable media that stores data for short periods of time like register memory, processor cache and Random Access Memory (RAM). The computer readable medium may also include non-transitory media, such as secondary or persistent long-term storage, like read only memory (ROM), optical or magnetic disks, compact-disc read only memory (CD-ROM), for example. The computer readable media may also be any other volatile or non-volatile storage systems. The computer readable medium may be considered a tangible computer readable storage medium, for example.

In addition, each block or portions of each block in FIG. 10, and within other processes and methods disclosed herein, may represent circuitry that is wired to perform the specific logical functions in the process. Alternative implementations are included within the scope of the examples of the present disclosure in which functions may be executed out of order from that shown or discussed, including substantially concurrent or in reverse order, depending on the functionality involved, as would be understood by those reasonably skilled in the art.

At block 1002, the method 1000 includes displaying, by a defibrillator, a user interface screen that includes a primary channel for displaying a primary waveform and a secondary channel for displaying secondary data. The defibrillator includes a therapy cable receptacle configured to receive a therapy cable comprising therapy pads, and an ECG cable receptacle configured to receive an ECG electrode cable. In some examples, the primary channel is positioned above the secondary channel.

At block 1004, the method 1000 includes detecting, by the defibrillator, a lack of a patient connection for therapy pads. In some examples, detecting the lack of the patient connection for the therapy pads includes measuring a patient impedance using the therapy pads, and determining that the patient impedance satisfies a threshold condition.

At block 1006, the method 1000 includes detecting, by the defibrillator, a patient connection for an ECG lead. The ECG lead is obtained using an ECG electrode cable. In some examples, detecting the patient connection for the ECG lead includes measuring a patient impedance using the ECG electrode cable, and determining that the patient impedance satisfies a threshold condition. Additionally or alternatively, detecting the patient connection for the ECG lead can include determining that multiple electrodes of the ECG electrode cable are connected to a patient.

And at block 1008, the method 1000 includes, based on detecting the lack of the patient connection for the therapy pads and detecting the patient connection for the ECG lead, displaying, by the defibrillator, a representation of an ECG signal obtained using the ECG electrode cable in the primary channel. In some examples, the representation of the ECG signal is a representation of an ECG signal for the ECG lead. Further, the ECG lead can be a bipolar limb lead. In other examples, the representation of the ECG signal is a representation of an ECG signal for another ECG lead.

In some examples, the method 1000 further includes displaying a placeholder for a representation of an ECG signal obtained using the therapy pads in the primary channel prior to displaying the representation of the ECG signal obtained using the ECG electrode cable in the primary channel. With this arrangement, displaying the representation of the ECG signal obtained using the ECG electrode cable in the primary channel includes replacing the placeholder with the representation of the ECG signal obtained using the ECG electrode cable.

In some examples, the method 1000 further includes obtaining physiologic monitoring data using a sensor connected to the defibrillator and determining that the physiologic monitoring data satisfies a threshold condition. Further, the displaying of the representation of the ECG signal obtained using the ECG lead is further based on the determining that the physiologic monitoring data satisfies the threshold condition.

One advantage of switching the waveform displaying in the primary channel based on detecting a patient connection for an ECG lead obtained using the ECG electrode cable as opposed to detecting that an ECG electrode cable is connected to the ECG cable receptacle is that a user of the defibrillator can choose to always leave the ECG electrode cable connected to the defibrillator. This can reduce the number of times that the ECG electrode cable is plugged into and unplugged from the ECG cable receptacle over a life of the defibrillator, thereby improving a useable life of the ECG cable receptacle and or a connector of the ECG electrode cable. Similarly, the user of the defibrillator can choose to leave the therapy cable connected to the therapy cable receptacle, since the techniques for switching the waveform in the primary channel involve detecting a lack of a patient connection for the therapy pads as opposed to detecting that the therapy cable is connected to the therapy cable receptacle. Hence, the techniques described herein can also improve the usable life of the connector of the therapy cable and/or the therapy cable receptacle by reducing the number of times that the therapy cable is plugged into and unplugged from the therapy cable receptacle.

By the term "substantially" and "about" used herein, it is meant that the recited characteristic, parameter, or value need not be achieved exactly, but that deviations or variations, including for example, tolerances, measurement error, measurement accuracy limitations and other factors known to skill in the art, may occur in amounts that do not preclude the effect the characteristic was intended to provide.

Different examples of the system(s), device(s), and method(s) disclosed herein include a variety of components, features, and functionalities. It should be understood that the various examples of the system(s), device(s), and method(s) disclosed herein may include any of the components, features, and functionalities of any of the other examples of the system(s), device(s), and method(s) disclosed herein in any combination or any sub-combination, and all of such possibilities are intended to be within the scope of the disclosure.

The description of the different advantageous arrangements has been presented for purposes of illustration and description, and is not intended to be exhaustive or limited to the examples in the form disclosed. Many modifications and variations will be apparent to those of ordinary skill in the art. Further, different advantageous examples may describe different advantages as compared to other advantageous examples. The example or examples selected are chosen and described in order to best explain the principles of the examples, the practical application, and to enable others of ordinary skill in the art to understand the disclosure for various examples with various modifications as are suited to the particular use contemplated.

What is claimed is:

1. A method comprising:
   displaying, by a defibrillator, a user interface screen that includes a primary channel for displaying a primary waveform and a secondary channel for displaying secondary data, wherein the defibrillator comprises:
   a therapy cable receptacle configured to receive a therapy cable comprising therapy pads, and
   an electrocardiogram (ECG) cable receptacle configured to receive an ECG electrode cable;

detecting, by the defibrillator, a lack of a patient connection for the therapy pads;

detecting, by the defibrillator, a patient connection for an ECG lead, wherein the ECG lead is obtained using the ECG electrode cable; and based on detecting the lack of the patient connection for the therapy pads and detecting the patient connection for the ECG lead, displaying a representation of an ECG signal obtained using the ECG electrode cable in the primary channel.

2. The method of claim 1, wherein the primary channel is positioned above the secondary channel.

3. The method of claim 1, further comprising prior to displaying the representation of the ECG signal obtained using the ECG electrode cable in the primary channel, displaying a placeholder for a representation of an ECG signal obtained using the therapy pads in the primary channel, wherein displaying the representation of the ECG signal obtained using the ECG electrode cable in the primary channel comprises replacing the placeholder with the representation of the ECG signal obtained using the ECG electrode cable.

4. The method of claim 1, wherein detecting the lack of the patient connection for the therapy pads comprises:

measuring a patient impedance using the therapy pads; and determining that the patient impedance satisfies a threshold condition.

5. The method of claim 1, wherein detecting the patient connection for the ECG lead comprises:

measuring a patient impedance using the ECG electrode cable; and determining that the patient impedance satisfies a threshold condition.

6. The method of claim 1, wherein detecting the patient connection for the ECG lead comprises determining that multiple electrodes of the ECG electrode cable are connected to a patient.

7. The method of claim 1, further comprising:

obtaining physiologic monitoring data using a sensor connected to the defibrillator; and determining that the physiologic monitoring data satisfies a threshold condition, wherein displaying the representation of the ECG signal for the ECG lead in the primary channel is further based on determining that the physiologic monitoring data satisfies a threshold condition.

8. The method of claim 1, wherein the representation of the ECG signal is a representation of an ECG signal for the ECG lead.

9. The method of claim 8, wherein the ECG lead is a bipolar limb lead.

10. The method of claim 1, wherein the representation of the ECG signal is a representation of an ECG signal for another ECG lead.

11. A non-transitory computer-readable medium having stored therein a plurality of executable instructions, which when executed by a defibrillator causes the defibrillator to perform functions comprising:

displaying a user interface screen that includes a primary channel for displaying a primary waveform and a secondary channel for displaying secondary data, wherein the defibrillator comprises:

a therapy cable receptacle configured to receive a therapy cable comprising therapy pads, and an electrocardiogram (ECG) cable receptacle configured to receive an ECG electrode cable;

detecting a lack of a patient connection for the therapy pads;

detecting a patient connection for an ECG lead, wherein the ECG lead is obtained using the ECG electrode cable; and based on detecting the lack of the patient connection for the therapy pads and detecting the patient connection for the ECG lead, displaying a representation of an ECG signal obtained using the ECG electrode cable in the primary channel.

12. The non-transitory computer-readable medium of claim 11, wherein the primary channel is positioned above the secondary channel.

13. The non-transitory computer-readable medium of claim 11, wherein:

the functions further comprise prior to displaying the representation of the ECG signal obtained using the ECG electrode cable in the primary channel, displaying a placeholder for a representation of an ECG signal obtained using the therapy pads in the primary channel, and displaying the representation of the ECG signal obtained using the ECG electrode cable in the primary channel comprises replacing the placeholder with the representation of the ECG signal obtained using the ECG electrode cable.

14. The non-transitory computer-readable medium of claim 11, wherein detecting the lack of the patient connection for the therapy pads comprises:

measuring a patient impedance using the therapy pads; and determining that the patient impedance satisfies a threshold condition.

15. The non-transitory computer-readable medium of claim 11, wherein detecting the patient connection of the ECG lead comprises:

measuring a patient impedance using the ECG electrode cable; and determining that the patient impedance satisfies a threshold condition.

16. The non-transitory computer-readable medium of claim 11, where detecting the patient connection for the ECG lead comprises determining that multiple electrodes of the ECG electrode cable are connected to a patient.

17. A defibrillator comprising:

a therapy cable receptacle configured to receive a therapy cable comprising therapy pads;

an electrocardiogram (ECG) cable receptacle configured to receive an ECG electrode cable;

a non-transitory computer-readable medium having stored therein a plurality of executable instructions; and a processor adapted to execute the plurality of executable instructions to:

display a user interface screen that includes a primary channel for displaying a primary waveform and a secondary channel for displaying secondary data, detect a lack of a patient connection for the therapy pads;

detect a patient connection for an ECG lead, wherein the ECG lead is obtained using the ECG electrode cable; and based on detecting the lack of the patient connection for the therapy pads and detecting the patient connection for the ECG lead, display a representation of an ECG signal obtained using the ECG electrode cable in the primary channel.

18. The defibrillator of claim 17, wherein the primary channel is positioned above the secondary channel.

19. The defibrillator of claim 17, wherein detecting the lack of the patient connection for the therapy pads comprises:
   measuring a patient impedance using the therapy pads; and
   determining that the patient impedance satisfies a threshold condition.

20. The defibrillator of claim 17, wherein detecting the patient connection for the ECG lead comprises:
   measuring a patient impedance using the ECG electrode cable; and
   determining that the patient impedance satisfies a threshold condition.

* * * * *